| United States Patent [19] | [11] | 4,332,740 |
|---|---|---|
| Kato et al. | [45] | Jun. 1, 1982 |

[54] PROCESS FOR PREPARING PEROXYESTERS

[75] Inventors: Kenji Kato, Kariya; Hidehiko Hagii, Aichi, both of Japan

[73] Assignee: Nippon Oil and Fats Co., Ltd., Tokyo, Japan

[21] Appl. No.: 223,551

[22] Filed: Jan. 9, 1981

[30] Foreign Application Priority Data

Jan. 19, 1980 [JP] Japan .................................. 55-4755

[51] Int. Cl.$^3$ .......................................... C07C 179/02
[52] U.S. Cl. ............................................ 260/453 RZ
[58] Field of Search ................................. 260/453 RZ

[56] References Cited

U.S. PATENT DOCUMENTS 2,567,615  9/1951  Milas ............................ 260/453 RZ
3,082,236  3/1963  Mageli et al. ................. 260/453 RZ

OTHER PUBLICATIONS

Noller, Textbook of Organic Chemistry, W. B. Saunders Co., Philadelphia, 1958, pp. 128, 129.

*Primary Examiner*—John M. Ford
*Assistant Examiner*—Robert C. Whittenbaugh
*Attorney, Agent, or Firm*—Blanchard, Flynn, Thiel, Boutell & Tanis

[57] ABSTRACT

A high concentration of an aqueous potassium hydroxide is reacted with a hydroperoxide, whereby obtaining a potassium salt of the hydroperoxide is obtained.

This potassium hydroperoxide salt can be reacted with an acid halide in a homogeneous reaction system in the presence of non-polar organic solvents, thereby obtaining a non-polar organic solvent solution of novel peroxyesters in high concentration and in high yield.

5 Claims, No Drawings

PROCESS FOR PREPARING PEROXYESTERS

This invention relates to a process for preparing a peroxyester shown by the formula,

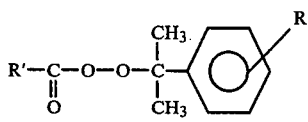

wherein R is a $C_1$-$C_4$ linear or branched alkyl group positioned in a meta—or para-position on the aromatic nucleus and R' represents a $C_1$-$C_{12}$ linear or branched alkyl group, a phenyl group or a substituted phenyl group.

While peroxyesters similar to those shown by the formula,

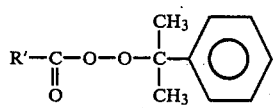

are known substances, peroxyesters shown by the above described formula,

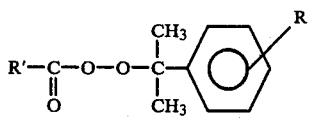

are novel substances, which are useful as polymerization initiators for vinyl monomers, especially for homo- or copolymerization of vinyl chloride monomers carried out at a relatively low temperature, and as hardening agents or cross-linking agents for polyester resins.

Processes for producing peroxyesters are roughly classified into the three processes discussed below.

The first process has the essential feature that a hydroperoxide is reacted with an acid halide in the presence of an organic base such as pyridine. There is difficulty in the industrial application of this process. The steps for purifying the product are complex because the process requires recovery of costly pyridine having had odour and further to separation of pyridine remaining in the peroxyesters.

The second process comprises reacting a hydroperoxide with an acid halide in the presence of an inorganic base such as alkali metal hydroxide in a heterogeneous reaction system, as described in U.S. Pat. No. 2,567,615. However, this process may be hardly usable for industrial production because the process has the drawback of low production yield due to formation of by-products. Since the reaction is carried out in a reaction system of high viscosity and in a slurry state, it is difficult to homogeneously agitate the reaction system, and it is difficult to maintain effective temperature control at the optimum reaction temperature because of the large exothermic heat released by the reaction.

The third process comprises preparing an aqueous solution of a hydroperoxide alkali metal salt in the first stage by reacting a hydroperoxide with 10-25% by weight aqueous solution of an alkali metal hydroxide as the inorganic base, and then, in a second stage, adding a halide into the reaction product of the first stage to react with the resulting heterogeneous reaction mixture.

An example of this process is a process for producing an α-cumyl peroxyester as disclosed in Japanese examined patent application publication No. 3847/1979.

This third process shows a good workability and is actually used.

However, production of the above stated peroxyesters shown by the general formula (III)

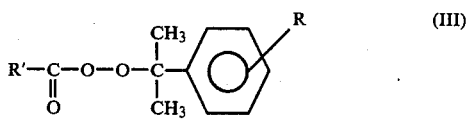

has not been successful according to the process of the third process, because no substantial reaction takes place between a hydroperoxide shown by the general formula (I)

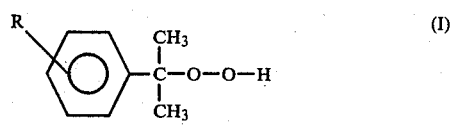

and sodium hydroxide when they are mixed with each other.

Further, addition of an acid halide to the resulting mixture composition fails to produce the desired peroxide.

Accordingly, it is seen that the peroxyesters shown by the above stated general formula (III) can be hardly produced according to the third process.

SUMMARY OF THE INVENTION

A main object of this invention is to provide a process for industrially producing novel peroxyesters shown by the above stated general formula (III).

This invention is based on the findings that an aqueous solution of potassium hydroxide, specified as the alkali metal hydroxide, can be reacted in a high concentration range with a hydroperoxide shown by the general formula (I) to easily produce a potassium salt of the hydroperoxide which is soluble in non-polar organic solvents, and that the potassium salt of the hydroperoxide and an acid halide, which is shown by the general formula of

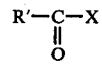

can be reacted with each other in a homogeneous reaction system by mixing a non-polar organic solvent solution of the potassium salt of hydroperoxide with the acid halide.

The novel peroxyester shown by the general formula (III) is produced by reacting a hydroperoxide shown by the general formula (I) with an aqueous solution of potassium hydroxide in the presence of a non-polar organic solvent, and then adding an acid halide shown by the general formula (II) into the resulting non-polar organic solvent solution of the potassium salt of hydroperoxide to react them.

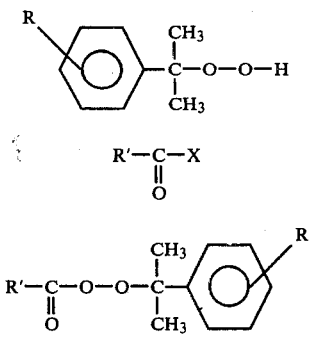

(I)

R'—C—X (II)
   ‖
   O (III)

In the formulas, R and R' have the same meanings as above.

This peroxyester is produced in the form of a solution diluted with the above stated non-polar organic solvent and usually sold in such a diluted solution form.

The above stated peroxyesters which can be prepared in the production process of this invention include, for example, 1-methyl-1-(p-or m-methylphenyl)ethyl peroxybenzoate, 1-methyl-1-(p-or m-ethylphenyl)ethyl peroxybenzoate 1-methyl-1-(p-or m-isopropylphenyl-)ethyl peroxybenzoate, 1-methyl-1-(p-or m-t-butylphenyl)ethyl peroxybenzoate, 1-methyl-1-(p-or m-methylphenyl)ethyl peroxy o-or m-toluate,1-methyl-1-(p-or m-ethylphenyl)ethyl peroxy o-or m-toluate, 1-methyl-1-(p-or m-isopropylphenyl)ethyl peroxy o-or m-toluate, 1-methyl-1-(p-or m-t-butylphenyl)ethyl peroxy o-or m-toluate, 1-methyl-1-(p-or m-methylphenyl)ethyl peroxyacetate, 1-methyl-1-(p-or m-ethylphenyl)ethyl peroxyacetate, 1-methyl-1-(p-or m-isopropylphenyl)ethyl peroxyacetate, 1-methyl-1-(p-or m-t-butylphenyl)ethyl peroxyacetate, 1-methyl-1-(p-or m-methylphenyl)ethyl peroxyisobutyrate, 1-methyl-1-(p-or m-ethylphenyl)ethyl peroxyisobutyrate, 1-methyl-1-(p-or m-isopropylphenyl)ethyl peroxyisobutyrate, 1-methyl-1-(p-or m-t-butylphenyl)ethyl peroxyisobutyrate, 1-methyl-1-(p-or m-methylphenyl)ethyl peroxy(2-ethyl)hexanoate, 1-methyl-1-(p-or m-ethylphenyl)ethyl peroxy(2-ethyl)hexanoate, 1-methyl-1-(p-or m-isopropylphenyl)ethyl peroxy(2-ethyl)hexanoate, 1-methyl-1-(p-or m-t-butylphenyl)ethyl peroxy(2-ethyl)hexanoate, 1-methyl-1-(p-or m-methylphenyl)ethyl peroxy (3,5,5-trimethyl) hexanoate, 1-methyl-1-(p-or m-ethylphenyl)ethyl peroxy (3,5,5-trimethyl)hexanoate, 1-methyl-1-(p-or m-isopropylphenyl)ethyl peroxy(3,5,5-trimethyl)hexanoate, 1-methyl-1-(p-or m-t-butylphenyl)ethyl peroxy (3,5,5-trimethyl)hexanoate, 1-methyl-1-(p-or m-methylphenyl)ethyl peroxylaurate, 1-methyl-1-(p-or m-ethylphenyl)ethyl peroxylaurate,1-methyl-1-(p-or m-isopropyl phenyl)ethyl peroxylaurate, 1-methyl-1-(p-or m-t-butylperoxy) ethyl peroxylaurate, 1-methyl-1-(p-or m-methylphenyl)ethyl peroxy pivalate, 1-methyl-1-(p-or m-ethylphenyl)ethyl peroxypivalate, 1-methyl-1-(p-or m-isopropylphenyl)ethyl peroxypivalate. 1-methyl-1-(p-or m-t-butylphenyl)ethyl peroxypivalate, 1-methyl-1-(p-or m-methylphenyl)ethyl peroxyneoheptanoate, 1-methyl-1-(p-or m-ethylphenyl)ethyl peroxyneoheptanoate, 1-methyl-1-(p-or m-isopropylphenyl)ethyl peroxyneoheptanoate, 1-methyl-1-(p-or m-t-butylphenyl)ethyl peroxyneoheptanoate, 1-methyl-1-(p-or m-methylphenyl)ethyl peroxyneooctanoate, 1-methyl-1-(p-or m-ethylphenyl)ethyl peroxyneooctanoate, 1-methyl-1-(p-or m-isopropylphenyl)ethyl peroxyneooctanoate, 1-methyl-1-(p-or m-t-butylphenyl)ethyl peroxyneooctanoate, 1-methyl-1-(p-or m-methylphenyl)ethyl peroxyneodecanoate, 1-methyl-1-(p-or m-ethylphenyl)ethyl peroxyneodecanoate, 1-methyl-1-(p-or m-isopropylphenyl)ethyl peroxyneodecanoate and 1-methyl-1-(p-or m-t-butylphenyl)ethyl peroxyneodecanoate.

The hydroperoxides of the above stated general formula (I) which are used for the production of the peroxyesters of this invention can be listed for example, as follows:

1-methyl-1-(p-or m-methylphenyl)ethyl hydroperoxide, 1-methyl-1-(p-or m-ethylphenyl)ethyl hydroperoxide, 1-methyl-1-(p-or m-isopropylphenyl)ethyl hydroperoxide and 1-methyl-1-(p-or m-t-butylphenyl)ethyl hydroperoxide.

The used amounts of the above stated hydroperoxides can be changed depending on the species of the acid halides which are reacted with the potassium salts of the hydroperoxides, but are usually within the range of 0.9 to 1.8 times stoichiometric amounts based on the acid halides.

The reason for specifying that the potassium hydroxide is in the aqueous solution when used as the alkali metal hydroxide to be reacted with the above stated hydroperoxides in this invention is that only the potassium salts of hydroperoxides are soluble in non-polar organic solvents and give homogeneous solutions.

In addition, the concentration of potassium hydroxide in the aqueous solution is restricted to 35 to 60% by weight.

The desired peroxyesters are scarcely produced when potassium hydroxide is used in a concentration less than 35% because the potassium salts of hydroperoxides are not formed in such a case. At the other extreme, it is difficult to prepare an aqueous solution of potassium hydroxide having a concentration more than 60% by weight.

Potassium hydroxide in the form of 35 to 60% by weight in aqueous solution is usually used in an amount ranging from 0.9 to 2.0 times stoichiometric amounts based on the hydroperoxide shown by the general formula (I).

Examples of the acid halides of the above stated general formula (II) are: benzoyl chloride, o-or m-methyl benzoyl chloride, acetyl chloride, isobutyryl chloride, 2-ethyl hexanoyl chloride, 3,5,5-trimethyl hexanoyl chloride, lauroyl chloride, povaloyl chloride, neoheptanoyl chloride, neooctanoyl chloride, neodecanoyl chloride and acid bromides corresponding to the above listed acid chlorides in which bromine atoms are introduced instead of chlorine atoms.

The non-polar solvents used in this invention are such solvents as aliphatic and aromatic hydrocarbons. It is not preferable to use a polar solvent because the peroxyesters are less stable during storage when they are diluted with polar solvents, and use of peroxyesters in a polymerization reaction after dilution with a polar solvent adversely affects the polymerization system.

Accordingly, use of polar solvents in the reaction complicates the production steps because it is necessary to remove the polar solvents from the final products.

Examples of non-polar organic solvents usable in the invention are: pentane, hexane, octane, petroleum naphtha, mineral spirits, mineral oils, benzene, toluene, xylene, isopropylbenzene, t-butylbenzene, diisopropylbenzene and mixtures of these non-polar organic solvents. These solvents are used in an amount within the range of 0.3 to 2 times an amount by weight based on the amounts of the acid halides used, and preferably in an amount so that the products will contain the product peroxyester in the amount of 50 to 80% by weight based on the total amount of the product obtained by the addition of the non-polar organic solvents. A high concentration of the peroxyesters diluted with the non-polar organic solvent of more than 80% by weight detracts from safty during handling and storage thereof and renders the dilution meaningless. A peroxyester concentration less than 50% by weight results in reduced vessel efficiency because excess amounts of the non-polar organic solvents exist in the total reaction liquid in the reaction.

The reaction conditions employed in the production process of this invention are usually as follows.

The reaction of the hydroperoxide and the potassium hydroxide aqueous solution is usually carried out at a temperature lower than 30° C. under cooling and stirring because the reaction is exothermic.

The reaction of the thus prepared potassium salts of the hydroperoxides dissolved in the non-polar organic solvents with the acid halides is usually carried out at a temperature within the range of −10° to 30° C. under stirring. The reaction time is usually within the range of 1 to 3 hours after both the reactants have been mixed.

The product non-polar organic solvent solutions of peroxyesters are effective for use as polymerization initiators for vinyl monomers, especially those for homo- or copolymerization of a vinyl chloride monomer, which is carried out at a relatively low temperature.

According to the production process of this invention, the above stated peroxyesters shown by the general formula (III) are produced in high yields with safety.

This production process is conducted in a homogeneous reaction system in a non-polar organic solvent and therefore temperature control of the system, for example by removing the reaction heat, is easily carried out. While by-products are produced in large amounts in the processes of heterogeneous reaction systems such as the conventional ones because the acid halides are in contact with water, the process of this invention makes it possible to reduce by-product production. Accordingly, purification steps are simplified because of the reduced by-product content and the peroxyesters diluted with the non-polar organic solvents can be directly sold commercially without steps such as distillation.

The production process of this invention is explained in more detail in the following Examples, Comparative Tests and Reference Examples.

EXAMPLE 1

Production of 1-methyl-1-(p-isopropylphenyl)ethyl peroxy pivalate

Into a four neck flask of 1 liter capacity were charged 194.3 g (1 mole) of 1-methyl-1-(p-isopropylphenyl)ethyl hydroperoxide and 100 g of mineral spirit which were maintained at 20° C. under stirring in an ice-water bath. Into the flask 224.0 g (2 moles) of a 50% by weight aqueous solution of potassium hydroxide were added dropwise during the course of 30 minutes.

After completion of the addition, agitation was further continued for 10 minutes to give a mineral spirit solution of a potassium salt of the above stated hydroperoxide.

Into the resulting homogeneous solution 132.7 g (1.1 moles) of pivaloyl chloride were added dropwise at 10° C. during the course of 30 minutes. After that the temperature was raised to 20° C. and the agitation was continued for another 1 hour.

Into the reaction mixture 300 ml of cold water were added and which settled to separate the organic layer, which was then recovered.

The organic layer was washed with 100 ml of 5% by weight aqueous solution of potassium hydroxide and then with cold water.

Thus resulting organic layer was dried with anhydrous magnesium sulfate to yield 320.0 g of a peroxyester solution, which had active oxygen due to the peroxyester in the amount of 3.95%. The product solution was a mineral spirit solution containing the peroxyester in an amount of 68.8% by weight, since the theoretical value of the active oxygen content in the peroxyester was 5.75%. The yield of the peroxyester was 79.0% per mole, based on the hydroperoxide.

IR analysis thereof showed absorptions at 1760 and 1772 cm$^{-1}$ due to carbonyl groups of the peroxyester.

Accordingly, it was found that the prepared peroxyester was 1-methyl-1-(p-isopropylphenyl)ethyl peroxypivalate.

EXAMPLE 2

A mineral spirit solution of the hydroxyperoxide potassium salt was prepared in the same way as in Example 1 except that 320.0 g (2 moles) of a 35% by weight aqueous solution of potassium hydroxide were used instead of the 50% by weight aqueous solution of potassium hydroxide.

Settling of the solution resulted in phase separation. After removal of the aqueous phase, the organic phase was subjected to the treatments in the same way as in Example 1 to give 267.8 g of a peroxyester solution. The solution had active oxygen due to the peroxyester in an amount of 3.60%.

Accordingly, the product solution was a mineral spirit solution containing the peroxyester in the amount of 62.7% by weight. The yield of 1-methyl-1-(p-isopropylphenyl)eth peroxypivalate was 60.3% per mole based on the hydroperoxide.

EXAMPLE 3

Production of the peroxyester solution was carried out in the same way as in Example 1 except that 186.7 g (2 moles) of a 60% by weight aqueous solution of potassium hydroxide were used instead of the 50% by weight aqueous solution of potassium hydroxide. As a result, 322.0 g of a peroxyester solution having active oxygen due to the peroxyester in the amount of 3.96% were obtained.

Accordingly, the product solution was a mineral spirit solution containing the peroxyester in the amount of 68.9% by weight. The yield of 1-methyl-1-(p-isopropylphenyl)ethyl peroxypivalate was 79.8% per mole based on the hydroperoxide.

EXAMPLE 4

Production of the peroxyester was carried out in the same way as in Example 1 except that toluene was used instead of the mineral spirit. As the result, 316.3 g of a peroxyester solution having active oxygen due to the peroxyester in the amount of 3.99% were obtained. Accordingly, the product solution was a toluene solution containing the peroxyester in the amount of 69.4% by weight. The yield of 1-methyl-1-(p-isopropylphenyl)ethyl peroxypivalate was 78.9% per mole based on the hydroperoxide.

COMPARATIVE TEST 1

Production of 1-methyl-1-(p-isopropylphenyl)ethyl peroxypivalate according to a conventional production process.

Into a four neck flask of 2 l capacity were charged 747.0 g (2 moles) of a 15% by weight aqueous solution of potassium hydroxide and 250 ml of t-butanol and the obtained mixture was maintained at 20° C. under stirring.

Into the flask 194.3 g (1 mole) of 1-methyl-1-(p-isopropylphenyl)ethyl hydroperoxide was added dropwise during the course of 30 minutes, during which time no appreciable release of exothermic heat was observed.

After completion of the addition, agitation was further continued for 10 minutes. Settlement of the reaction mixture showed a phase separation. Into the mixture 132.7 g (1.1 moles) of pivaloyl chloride was added dropwise at 10° C. under vigorous agitation during the course of 30 minutes. After that the temperature was raised to 20° C. and the agitation was continued for another 3 hours.

The organic layer was taken out and its active oxygen content was measured. As a result, the content of active oxygen due to the peroxyester was 0.2%.

Accordingly, the peroxyester of this invention could not substantially be produced according to the conventional process for producing peroxyesters.

COMPARATIVE TEST 2

A production process was carried out in the same way as in Comparative Test 1 except that 373.0 g (2 moles) of a 30% by weight aqueous solution of potassium hydroxide were used instead of the 15% by weight aqueous solution of potassium hydroxide.

The content of active oxygen due to the peroxyester in the resultant organic layer was 0.2%. Accordingly, the peroxyester of this invention could not substantially be produced as in Comparative Test 1.

COMPARATIVE TEST 3

A production process was carried out in the same way as in Comparative Test 1 except that 533.0 g (2 moles) of a 15% by weight aqueous solution of sodium hydroxide were used instead of the 15% by weight aqueous solution of potassium hydroxide.

The content of active oxygen due to the peroxyester in the resulting organic layer was 0.2%. Accordingly, the peroxyester of this invention could not substantially be produced.

COMPARATIVE TEST 4

A production process was carried out in the same way as in Comparative Test 1 except that t-butanol was not used. As the result, the content of active oxygen due to the peroxyester in the resulting organic layer was 0.2%. Accordingly, the peroxyester of this invention could not substantially be produced, according to the conventional method.

COMPARATIVE TEST 5

A formation reaction of a sodium salt of hydroperoxide was carried out as in Example 1 except that 160.0 g (2 moles) of 50% by weight aqueous solution of sodium hydroxide were used instead of the 50% by weight aqueous solution of potassium hydroxide. White crystals were deposited when the 50% by weight aqueous solution of sodium hydroxide was added into the mixture solution of the hydroperoxide and the mineral spirit.

After the completion of the addition, it was difficult to carry out the agitation because the white crystals were deposited in the flask in a large amount. Addition of 200 g of the mineral spirit could not dissolve or disperse the crystals.

Accordingly, further steps were abandoned because it was difficult to carry them out.

COMPARATIVE TEST 6

A formation reaction of the potassium salt of hydroperoxide was carried out in the same way as in Example 1 except that the non-polar organic solvent of this invention was not used.

The potassium salt of hydroperoxide was formed, which, however, was in a colloidal state when the 50% by weight aqueous solution of potassium hydroxide was added to the hydroperoxide, and it was difficult to carry out homogeneous agitation.

Accordingly, further steps were abandoned because it was difficult to carry them out.

EXAMPLE 5

Production of 1-methyl-1-(m-isopropylphenyl)ethyl peroxy neodecanoate

Into a four neck flask of 1 l capacity were charged 213.7 g (1.1 moles) of 1-methyl-1-(m-isopropylphenyl)ethyl hydroperoxide and 100 g of toluene, and these were maintained at 20° C. under stirring in an ice-water bath. Into the flask 224.0 g (2 moles) of a 50% by weight aqueous solution of potassium hydroxide were added dropwise during the course of 30 minutes.

After completion of the addition, agitation was continued for 10 minutes to give a toluene solution of potassium salt of the above stated hydroperoxide. Into the resultant homogeneous solution were added 190.7 g (1 mole) of neodecanoyl chloride dropwise at 20° C. during the course of 30 minutes.

The temperature was then raised to 30° C. and the agitation was continued for another 1 hour. Then the subsequent purification steps were carried out in the same way as in Example 1. As the result, 361.0 g of a solution of the peroxyester which had active oxygen due to the peroxyester in the content of 3.32% were obtained. Therefore, the product solution was a toluene solution containing the peroxyester in the amount of 72.3% by weight, since the theoretical value of the active oxygen content in the peroxyester was 4.59%.

The yield of the peroxyester was 75.0% per mole based on the neodecanoyl chloride employed. IR analysis showed absorptions at 1760 and 1770 cm$^{-1}$ due to the carbonyl group of the peroxyester.

Accordingly, the prepared peroxyester was 1-methyl-1-(m-isopropylphenyl)ethyl peroxyneodecanoate.

EXAMPLE 6 TO 18

Various peroxyesters were prepared as in Example 1 except that the hydroperoxides and acid halides shown in Table 1 were used, and reaction temperature of 20° C. was employed as in Example 13. Results are shown in Table 1.

REFERENCE EXAMPLE 1

Suspension polymerization of vinyl chloride

Suspension polymerization of vinyl chloride was carried out by using as the polymerization initiator 1-methyl-1-(p-isopropylphenyl)ethyl peroxypivalate, one of the peroxyesters of this invention. Polymerization procedures were as follows.

Into an autoclave made of stainless steel and having an inner volume of 300 ml were charged 100 ml of an aqueous solution containing 0.15 g of dissolved polyvinyl alcohol. Into the autoclave were further introduced 50 g of vinyl chloride monomer and 0.03 g of the above stated peroxyester. After the substitution of air existing in the gas present in the autoclave with the vinyl chloride monomer gas by the slight evaporation of the introduced vinyl chloride monomer, the autoclave was closed and set in a thermostat such that polymerization was carried out at 50°±1° C. for 6 hours.

After the polymerization, the resultant polyvinyl chloride powder was recovered and then washed with water, filtered, dried under vacuum and weighed. It was found that the conversion for polymerization was 66%.

REFERENCE EXAMPLE 2

Suspension polymerization of vinyl chloride

Suspension polymerization was carried out in the same way as in Reference Example 1 except that the polymerization initiator was 1-methyl-1-(p-isopropylphenyl)ethyl peroxyneodecanoate, which was one of the peroxyesters of this invention.

As the result, it was found that the conversion for polymerization was 78%.

The embodiments of the invention in which exclusive property or privilege is claimed are defined as follows:

1. A process for preparing a peroxyester of the formula

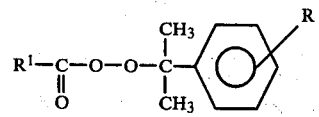

wherein R is a $C_1$ to $C_4$ linear or branched alkyl located in meta or para position on the benzene ring, and $R^1$ is selected from the group consisting of $C_1$ to $C_{12}$ linear or branched alkyl, phenyl and substituted phenyl, which consists essentially of the steps of:

1. in a first reaction stage, mixing a hydroperoxide of the formula

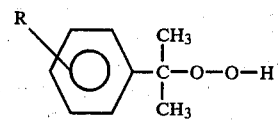

wherein R has the same meaning as defined above, with an aqueous potassium hydroxide solution containing from 35 to 60% by weight of potassium hydroxide and with a non-polar organic solvent, under conditions effective to form a homogeneous

TABLE 1

| Example No. | Hydroperoxide Species | Hydroperoxide Amount (mole) | Acid halide Species | Acid halide Amount (mole) | Amount of KOH in 50 wt % aqueous solution (mole) | Solvent Species | Solvent Amount (g) | Product peroxyester Species | Content of active oxygen (%) | Yield (% by mole) |
|---|---|---|---|---|---|---|---|---|---|---|
| 6 | 1-Methyl-1-(p-methylphenyl)ethyl hydroperoxide | 0.1 | Acetyl chloride | 0.13 | 0.15 | Toluene | 10 | 1-Methyl-1-(p-methylphenyl)ethyl peroxyacetate | 4.51 | 62.0 |
| 7 | 1-Methyl-1-(p-methylphenyl)ethyl hydroperoxide | 0.11 | Benzoyl chloride | 0.1 | 0.12 | Toluene | 10 | 1-Methyl-1-(p-methylphenyl)ethyl peroxybenzoate | 4.27 | 88.2 |
| 8 | 1-Methyl-1-(m-ethylphenyl)ethyl hydroperoxide | 0.11 | Iso-Butyl chloride | 0.1 | 0.12 | Mineral sprit | 10 | 1-Methyl-1-(m-ethylphenyl)ethyl peroxyisobutylate | 4.11 | 72.8 |
| 9 | 1-Methyl-1-(m-ethylphenyl)ethyl hydroperoxide | 0.11 | 2-Ethylhexanoyl chloride | 0.1 | 0.12 | Mineral sprit | 10 | 1-Methyl-1-(m-ethylphenyl)ethyl peroxy(2-ethyl)hexanoate | 3.84 | 84.3 |
| 10 | 1-Methyl-1-(p-isopropylphenyl)ethyl hydroperoxide | 0.11 | Benzoyl chloride | 0.1 | 0.12 | Mineral sprit | 10 | 1-Methyl-1-(p-isopropylphenyl)ethyl peroxybenzoate | 3.60 | 90.5 |
| 11 | 1-Methyl-1-(p-t-butylphenyl)ethyl hydroperoxide | 0.11 | 3,5,5-Trimethylhexanoyl chloride | 0.1 | 0.12 | Mineral sprit | 10 | 1-Methyl-1-(p-t-butylphenyl)ethyl peroxy(3,5,5-trimethyl)hexanoate | 3.52 | 86.2 |
| 12 | 1-Methyl-1-(p-t-butylphenyl)ethyl hydroperoxide | 0.11 | m-Methyl benzoyl chloride | 0.1 | 0.12 | Toluene | 10 | 1-Methyl-1-(p-t-butylphenyl)ethyl peroxy(m-methyl)benzoate | 3.69 | 90.3 |
| 13 | 1-Methyl-1-(p-t-butylphenyl)ethyl hydroperoxide | 0.11 | Neooctanoyl chloride | 0.1 | 0.12 | Toluene | 10 | 1-Methyl-1-(p-t-butylphenyl)ethyl peroxyneooctanoate | 3.43 | 75.6 | solution of the potassium salt of said hydroperoxide dissolved in said non-polar organic solvent, then 2. in a second reaction stage, mixing an acid halide of the formula

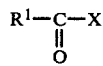

wherein $R^1$ has the same meaning as defined above and X is a halogen, with said homogeneous solution of said potassium salt of said hydroperoxide in said non-polar organic solvent, under conditions effective to form a solution containing from 50 to 80% by weight of said peroxyester dissolved in said non-polar organic solvent, and then 3. recovering said solution of said peroxyester dissolved in said non-polar organic solvent.

2. A process as claimed in claim 1, wherein the amount of said hydroperoxide used is 0.9 to 1.8 times the stoichiometric amount based on said acid halide, the amount of potassium hydroxide used is from 0.9 to 2.0 times the stoichiometric amount based on said hydroperoxide, the amount of said non-polar organic solvent used is from 0.3 to 2 times the amount of said acid halide, the reaction temperature of the first reaction stage is below 30° C., and the reaction temperature of the second reaction stage is −10° to 30° C.

3. A process as claimed in claim 2, wherein the non-polar organic solvent is selected from the group consisting of pentane, hexane, octane, petroleum naphtha, mineral spirits, mineral oils, benzene, toluene, xylene, isopropylbenzene, t-butylbenzene, diisopropylbenzene and mixtures thereof.

4. A process as claimed in claim 1, wherein said hydroperoxide is selected from the group consisting of 1-methyl-1-(p- or m-methylphenyl)ethyl hydroperoxide, 1-methyl-1-(p- or -m-ethylphenyl)ethyl hydroperoxide, 1-methyl-1-(p- or m-isopropylphenyl)ethyl hydroperoxide and 1-methyl-1-(p- or m-t-butylphenyl)ethyl hydroperoxide.

5. A process as claimed in claim 4, wherein the acid halide (11) is selected from the group consisting of benzoyl chloride, o- or m-methyl benzoyl chloride, acetyl chloride, isobutyryl chloride, 2-ethyl hexanoyl chloride, 3,5,5-trimethyl hexanoyl chloride, lauroyl chloride, pivaloyl chloride, neoheptanoyl chloride, neooctanoyl chloride, neodecanoyl chloride and acid bromides corresponding to the aforementioned acid chlorides.

* * * * *